(12) United States Patent
Kovalsky et al.

(10) Patent No.: US 9,918,833 B2
(45) Date of Patent: Mar. 20, 2018

(54) PROSTHETIC VALVE SUPPORT STRUCTURE

(75) Inventors: Igor Kovalsky, Mounds View, MN (US); Yossi Tuval, Netanya (IL)

(73) Assignee: Medtronic Vascular Galway, Galway (IE)

( * ) Notice: Subject to any disclaimer, the term of this patent is extended or adjusted under 35 U.S.C. 154(b) by 1397 days.

(21) Appl. No.: 13/216,533

(22) Filed: Aug. 24, 2011

(65) Prior Publication Data

US 2012/0053682 A1 Mar. 1, 2012

Related U.S. Application Data

(60) Provisional application No. 61/379,115, filed on Sep. 1, 2010.

(51) Int. Cl.
*A61F 2/24* (2006.01)

(52) U.S. Cl.
CPC .... *A61F 2/2418* (2013.01); *A61F 2220/0016* (2013.01); *A61F 2230/0054* (2013.01); *A61F 2250/0048* (2013.01)

(58) Field of Classification Search
CPC ............ A61F 2/2418; A61F 2200/0016; A61F 2230/0054; A61F 2250/0048
USPC ................... 623/1.24–1.26, 1.32, 2.17–2.18, 623/1.13–1.33
See application file for complete search history.

(56) References Cited

U.S. PATENT DOCUMENTS

| | | | |
|---|---|---|---|
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 3,795,246 A | 3/1974 | Sturgeon | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos | |
| 4,291,420 A | 9/1981 | Reul | |
| 4,297,749 A | 11/1981 | Davis et al. | |
| 4,339,831 A | 7/1982 | Johnson | |
| 4,343,048 A | 8/1982 | Ross et al. | |

(Continued)

FOREIGN PATENT DOCUMENTS

| | | |
|---|---|---|
| CN | 101011298 | 8/2007 |
| DE | 3640745 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Sarah W Aleman
(74) *Attorney, Agent, or Firm* — Medler Ferro Woodhouse & Mills PLLC

(57) ABSTRACT

The present invention is directed to prostheses including a support structure having a proximal end and a distal end, and a motion limiting member attached to the distal end of the support structure, wherein the motion limiting member is configured to restrict radial expansion of the distal end of the support structure. Methods for delivering the prosthesis are also provided.

2 Claims, 6 Drawing Sheets

(56) References Cited

U.S. PATENT DOCUMENTS

| | | |
|---|---|---|
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,665,906 A | 5/1987 | Jervis |
| 4,681,908 A | 7/1987 | Broderick et al. |
| 4,710,192 A | 12/1987 | Liotta et al. |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,037,434 A | 8/1991 | Lane |
| 5,047,041 A | 9/1991 | Samuels |
| 5,059,177 A | 10/1991 | Towne et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,217,483 A | 7/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,861,028 A | 1/1999 | Angell |
| 5,876,448 A | 3/1999 | Thompson et al. |
| 5,891,191 A | 4/1999 | Stinson |
| 5,906,619 A | 5/1999 | Olson et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,104 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 * | 9/2002 | Schreck ................ 623/2.18 |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |

(56) References Cited

U.S. PATENT DOCUMENTS

| | | |
|---|---|---|
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,806,919 B2 | 10/2010 | Bloom et al. |
| 2001/0002445 A1 | 3/2001 | Vesely |
| 2001/0000188 A1 | 4/2001 | Lenker et al. |
| 2001/0001314 A1 | 5/2001 | Davison et al. |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1* | 2/2003 | Gabbay .................. 623/2.11 |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |

(56) References Cited

U.S. PATENT DOCUMENTS

| | | |
|---|---|---|
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0149360 A1 | 7/2006 | Schwammenthal et al. |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |

(56) References Cited

U.S. PATENT DOCUMENTS

| | | |
|---|---|---|
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1* | 10/2008 | Guyenot et al. ............ 623/2.14 |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0036479 A1 | 2/2010 | Hill et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 815 | 4/2002 |
| EP | 1057460 A1 | 6/2000 |
| FR | 2788217 | 12/1999 |
| GB | 2056023 | 3/1981 |
| GB | 2433700 | 7/2007 |
| SU | 1271508 | 11/1986 |
| WO | 95/29640 | 11/1995 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | WO03/047468 | 6/2003 |
| WO | 04/019825 | 3/2004 |
| WO | 04/089250 | 10/2004 |
| WO | 05/002466 | 1/2005 |
| WO | 05/004753 | 1/2005 |
| WO | 05/046528 | 5/2005 |
| WO | 06/026371 | 3/2006 |
| WO | 06/070372 | 7/2006 |
| WO | 08/047354 | 4/2008 |
| WO | WO2008/070797 | 6/2008 |
| WO | 08/138584 | 11/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |
| WO | 09/111241 | 9/2009 |

OTHER PUBLICATIONS

Babaliaros, et al., "State of the Art Percutaneous Intervention for the Treatment of Valvular Heart Disease: A Review of the Current

(56) References Cited

OTHER PUBLICATIONS

Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine, Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal Sep. 22, 2001, p. 355
Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg., 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al., "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, pp. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Techol. 2000, vol. 9, pp. 287-292.

* cited by examiner

PROSTHETIC VALVE SUPPORT STRUCTURE

RELATED APPLICATION DATA

This application claims priority to U.S. Provisional Patent Application No. 61/379,115, filed Sep. 1, 2010.

BACKGROUND OF THE INVENTION

Field of the Invention

The present invention relates to prosthetic valves and methods for their implantation. More particularly, the present invention provides for prosthetic valve support structures configured for transcatheter delivery.

Background

Aortic valve replacement in patients with severe valve disease is a common surgical procedure. The replacement is conventionally performed by open heart surgery, in which the heart is usually arrested and the patient is placed on a heart bypass machine. Prostheses including prosthetic heart valves have been developed that are implanted using minimally invasive procedures such as transapical or percutaneous approaches. These methods involve compressing the prosthesis radially to reduce its diameter, inserting the prosthesis into a delivery tool, such as a catheter, and advancing the delivery tool to the correct anatomical position in the heart. Once properly positioned, the prosthesis is deployed by radial expansion within the native valve annulus.

Such a prosthesis can include a support structure to maintain the prosthetic heart valve in place. The inflow section of the prosthesis can be subject to radial interference from a body lumen, such as the left ventricular outflow tract (LVOT), that can exert circumferential radial pressure on the prosthesis. Such radial interference at an inflow section of the prosthesis can result in radial movement at an outflow section of the prosthesis. Such movement may be undesirable.

Moreover, a prosthesis can be subject to radial movement at an inflow section, due to, for example, valve function and cardiac contraction. Such radial movement can cause the diameter of the inflow section to experience cyclical contraction and expansion. Such contraction and expansion can subject the prosthesis to unnecessary fatigue.

Additionally, due to less than perfect conformance between the geometries of a patient's anatomy and the prosthesis, paravalvular leakage can occur. For example, a major course of leakage between a prosthesis and the LVOT wall is due to spaces created between scalloped leaflets called inter-leaflet triangles.

Accordingly, there is a need for a prosthesis that provides decoupled radial motion of the outflow section and the inflow section, and that better conforms to a patient's anatomy.

PCT Publication No. WO 05/002466 to Schwammenthal et al., which is incorporated herein by reference in its entirety, describes prosthetic devices for treating aortic stenosis.

PCT Publication No. WO 06/070372 to Schwammenthal et al., which is incorporated herein by reference in its entirety, describes a prosthetic device having a single flow field therethrough, adapted for implantation in a subject, and shaped so as to define a fluid inlet, and a diverging section, distal to the fluid inlet.

U.S. Patent Application Publication No. 2006/0149360 to Schwammenthal et al., which is incorporated herein by reference in its entirety, describes a prosthetic device including a valve-orifice attachment member attachable to a valve in a blood vessel and including a fluid inlet, and a diverging member that extends from the fluid inlet, the diverging member including a proximal end near the fluid inlet and a distal end distanced from the proximal end. A distal portion of the diverging member has a larger cross-sectional area for fluid flow therethrough than a proximal portion thereof.

U.S. Patent Application Publication No. 2006/0259136 to Nguyen et al., which is incorporated herein by reference, describes a heart valve prosthesis having a self-expanding multi-level frame that supports a valve body including a skirt and plurality of coapting leaflets. The frame transitions between a contracted delivery configuration that enables percutaneous transluminal delivery, and an expanded deployed configuration having an asymmetric hourglass shape. The valve body skirt and leaflets are constructed so that the center of coaptation can be selected to reduce horizontal forces applied to the commissures of the valve, and to efficiently distribute and transmit forces along the leaflets and to the frame. Alternatively, the valve body can be used as a surgically implantable replacement valve prosthesis.

BRIEF SUMMARY OF THE INVENTION

The present invention provides a valve prosthesis support structure that limits radial motion at a distal end thereof.

The present invention also provides a valve prosthesis support structure that limits radial motion at a proximal end thereof.

The present invention also provides a valve prosthesis support structure that includes sealing members to prevent paravalvular leakage.

The present invention provides a prosthesis including a support structure having a proximal end and a distal end, and a motion limiting member attached to the distal end of the support structure, wherein the motion limiting member is configured to restrict radial expansion of the distal end of the support structure.

The present invention also provides a valve prosthesis support structure, including a collapsible and expandable support structure including a plurality of posts at a distal end thereof and a flared portion extending in a proximal direction from the plurality of posts, and a motion limiting member attached to a proximal end of the proximal skirt, wherein the motion limiting member is configured to restrict radial movement of the proximal end of the collapsible support structure.

The present invention also provides a method of delivering a prosthesis to a desired location in a body. One such method includes introducing a sheath of a delivery system into a subject's vasculature, wherein a distal tip of the sheath contains the prosthesis, advancing the distal tip of the sheath to the desired location in the body, and releasing the prosthesis within the body, wherein the prosthesis includes a support structure having a proximal end and a distal end, and a motion limiting member attached to the distal end of the support structure.

Additional features of the invention will be set forth in the description that follows. Both the foregoing general description and the following detailed description are exemplary and explanatory and are intended to provide further explanation of the invention as claimed.

BRIEF DESCRIPTION OF THE FIGURES

The accompanying figures, which are incorporated herein, form part of the specification and illustrate exemplary embodiments of the present invention. Together with the description, the figures further serve to explain the principles of and to enable a person skilled in the relevant art(s) to make and use the exemplary embodiments described herein. In the drawings like reference characters indicate identical or functionally similar elements.

DETAILED DESCRIPTION OF THE INVENTION

The following detailed description of the present invention refers to the accompanying figures that illustrate exemplary embodiments. Other embodiments are possible and may fall within the scope of the present invention. Modifications can be made to the exemplary embodiments described herein without departing from the spirit and scope of the present invention. Therefore, the following detailed description is not meant to be limiting. The operation and behavior of the exemplary embodiments presented are described with the understanding that various modifications and variations of the exemplary embodiments may be within the scope of the present invention.

Figure 1:
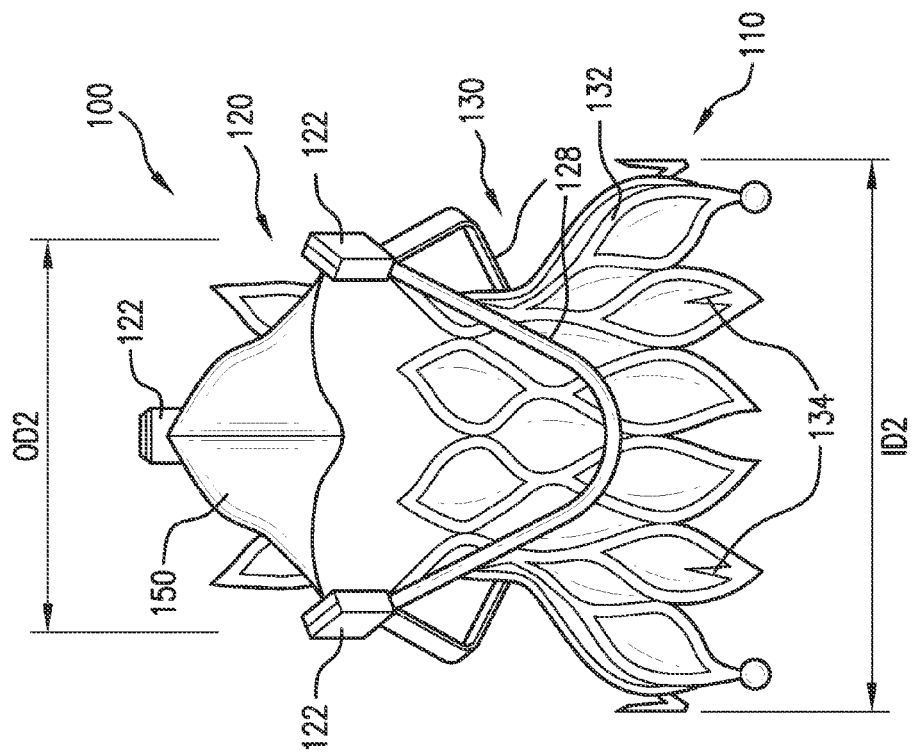
FIG. 1 is a perspective view of a valve prosthesis subject to radial interference at a proximal end.
Figure 2:
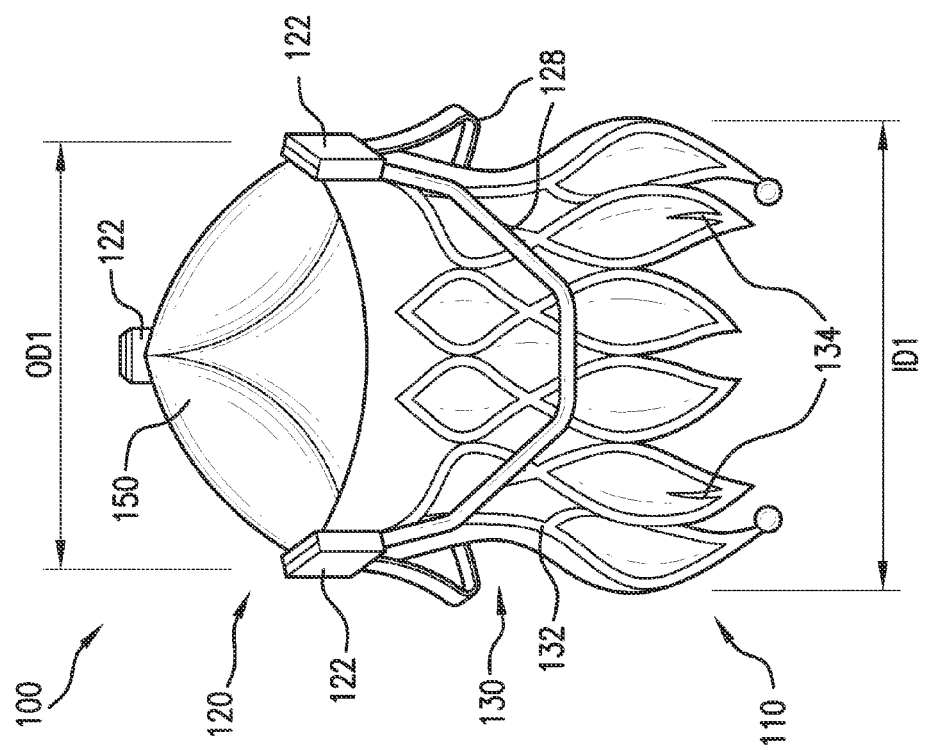
FIG. 2 is a perspective view of a valve prosthesis not subject to radial interference at a proximal end.

FIG. 1 is a perspective view of a valve prosthesis 100 subject to radial interference at a proximal end. Radial interference can constrain or cause a change in the diameter of a portion of valve prosthesis 100. FIG. 2 is a perspective view of valve prosthesis 100 not subject to radial interference at a proximal end. Valve prosthesis 100 includes an inflow section 110 at a proximal end thereof, and an outflow section 120 at a distal end thereof. Valve prosthesis 100 also includes a valve prosthesis support structure 130.

Valve prosthesis support structure 130 includes posts 122 (also referred to as commissural posts) proximate to outflow section 120, and a proximal skirt 132 extending from inflow section 110 toward posts 122.

Valve prosthesis 100 is preferably collapsible in order to facilitate transcatheter delivery. Preferably, valve prosthesis 100 can be delivered via a transfemoral approach. Valve prosthesis 100 can also be delivered, however, by other transvascular approach methods or a transapical approach. Valve prosthesis 100 can also be implanted by open heart surgery or related methods. The valve prosthesis 100 can expand radially upon delivery at a target site. The target site is preferably the native aortic annulus of a subject, but it is understood that valves according to the present invention could be implanted at other positions in a subject (e.g., a native mitral or pulmonary annulus).

For example, distal tip of a catheter sheath containing prosthesis 100 can be inserted into a patient's vasculature (e.g., via a body lumen such as a femoral artery) and advanced (along a guide wire, if provided) to the position of a native annulus. The native leaflets of the annulus can be in place at the time of implantation of prosthesis 100, or can be partially or completely removed prior to implantation. An outer tube of the catheter can be withdrawn some distance to expose a proximal portion of proximal skirt 132. The proximal portion can be positioned so as to abut against the ventricular side of the aortic annulus. If provided, barbs 134 can be primary contact points of prosthesis 100 with an interior of a valve retaining sleeve, thereby reducing friction that could be caused by the inner surface of the valve retaining sleeve sliding over prosthesis 100 while prosthesis 100 moves with respect to the catheter sheath. Once it is determined that prosthesis 100 is properly positioned in the annulus, the outer tube can be fully withdrawn, releasing valve prosthesis 100 and allowing radial expansion of valve prosthesis 100 to engage the annulus. If, after partial release, it is determined that the prosthesis is not properly positioned, the inflow section 110 can be recaptured into the outer tube for repositioning.

Prosthesis support structure 130 can be made of a self-expanding material, e.g., nitinol, thus tending toward a fully expanded position that is sufficient to securely engage the native annulus. When in position within a patient, this tendency creates a radial force between prosthesis support structure 130 and the patient's anatomy, thus helping to hold valve prosthesis 100 in place. The pressure applied by the prosthesis support structure 130, however, need not be sufficient by itself to anchor the prosthesis 100 in the native annulus. Further inhibiting migration of valve prosthesis 100 can be axial support arms 128, which protrude over the tips of the native leaflets to provide axial support to valve prosthesis 100 and to prevent valve prosthesis 100 from being forced into the ventricle through the native leaflets during the cardiac cycle. Support arms 128 can take on a variety of configurations. Further, as detailed above, inflow section 110 can engage the ventricle below the inflow end of the native annulus, providing additional anchoring.

Support arms 128 can, for example, be configured to be at least partially disposed within aortic sinuses of the subject, and, for some applications, to engage and/or rest against floors of the aortic sinuses, and to apply an axial force directed toward a left ventricle of the subject. Support arms 128 can meet one another at junctures. For applications in which each of support arms 128 is fabricated as a separate piece, the support arms can be mechanically engaged to one another where they meet at the junctures. For some applications, support arms 128 meet one another without actually touching one another, and instead meet via an area defined at each juncture. Typically, the support arms are configured to define peaks at the junctures, and troughs between adjacent peaks. U.S. application Ser. No. 11/728,253, filed Mar. 23, 2007, and U.S. application Ser. No. 11/726,889, filed Mar. 23, 2007 detail various support arm configurations, and each is incorporated by reference herein in its entirety.

In some exemplary embodiments, valve prosthesis 100 includes three posts 122, arranged circumferentially around a central longitudinal axis of valve prosthesis 100, and a flared portion extending in a proximal direction from posts 122. In some exemplary embodiments, valve prosthesis 100 includes more or fewer than three posts 122, such as, for example, two posts 122, or four posts 122. Approximately 90% of humans have exactly three aortic sinuses. The three posts 122 provided in some exemplary embodiments correspond to these three aortic sinuses. For implantation in the approximately 10% of patients that have exactly two aortic sinuses, valve prosthesis 100 can include only two posts 122.

Valve prosthesis 100 can also include a valve 150 coupled to posts 122. Valve 150 can be formed of a pliant material configured to collapse inwardly (i.e., towards the central longitudinal axis of valve prosthesis 100) during diastole, in order to inhibit retrograde blood flow, and to open outwardly during systole, to allow blood flow through valve prosthesis 100. Valve 150 can be formed of artificial or natural tissue. For example, valve 150 can be formed of bovine or porcine pericardium, or of any suitable synthetic material.

FIG. 2 is a perspective view of valve prosthesis 100 in an expanded state, wherein no inward radial pressure or interference is applied to inflow section 110. In this expanded state, inflow section 110 has a diameter ID2, and outflow section 120 has an outflow diameter OD2. FIG. 1 is a perspective view of a valve prosthesis 100 that is subject to inward radial pressure or interference at inflow section 110. Depending on the geometry of a particular subject's annulus, inflow section 110 will often be in at least a somewhat compressed position as shown in FIG. 1 due to the radial interference at inflow section 110. In this position, outflow section 120 has an outflow diameter OD1 that is larger than OD2, causing posts 122 to be positioned farther from one another than in a relaxed state. In other words, the outflow diameter of valve prosthesis 100 at outflow section 120 and the positioning of posts 122 are affected by radial interference on valve prosthesis 100 at inflow section 110, which can result in decreased performance characteristics of valve prosthesis 100.

Decoupling of radial motion of outflow section 120 from radial interference at inflow section 110 can produce significant benefits by providing more predictable and stable valve geometry regardless of patient-specific anatomy.

Figure 4:
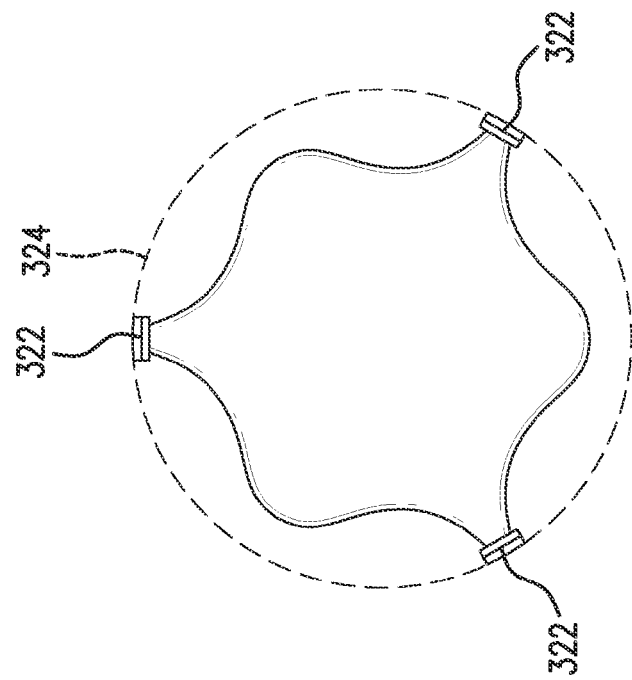
FIG. 4 is a top schematic view of the valve prosthesis of FIG. 3.
Figure 3:
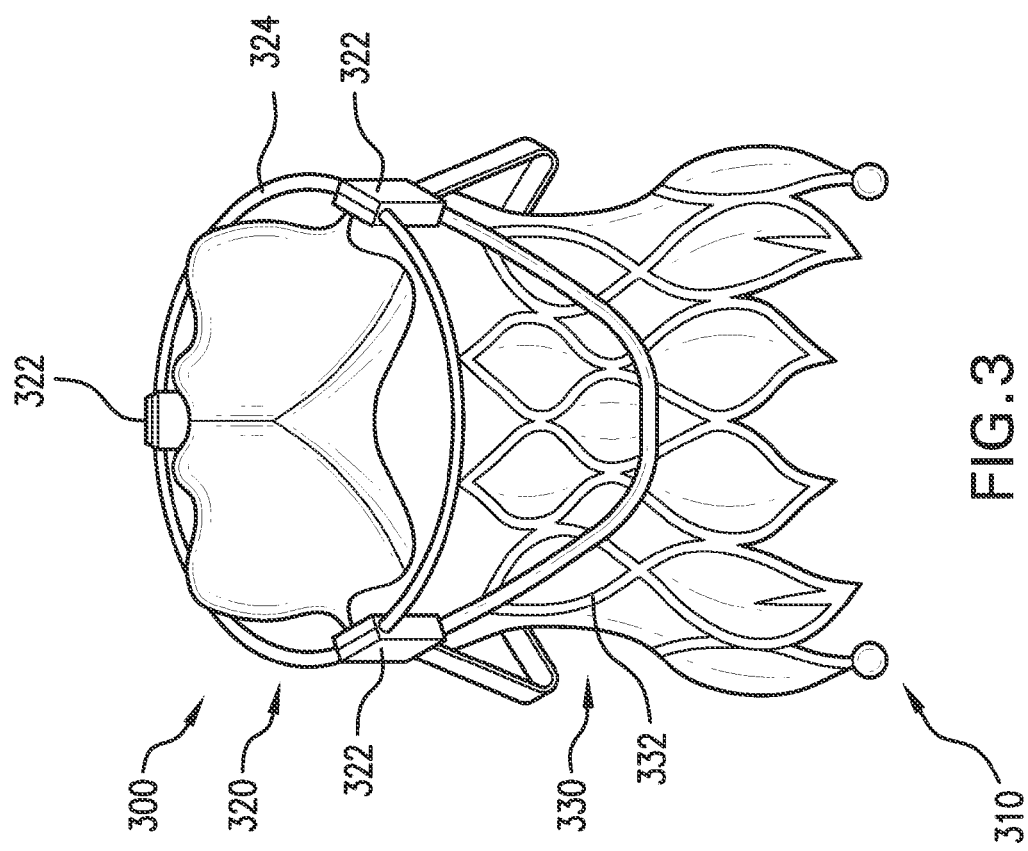
FIG. 3 is a perspective view of a valve prosthesis according to an embodiment of the present invention.

FIG. 3 is a perspective view of a valve prosthesis 300 according to an embodiment of the present invention. FIG. 4 is a top schematic view of valve prosthesis 300. The basic structure of valve prosthesis 300 is generally similar to valve prosthesis 100. Valve prosthesis 300 includes an inflow section 310 at a proximal end thereof, and an outflow section 320 at a distal end thereof. Valve prosthesis support structure 330 includes posts 322 proximate to outflow section 320, and a proximal skirt 332 extending from inflow section 310 towards posts 322. Valve prosthesis 300 also includes a valve prosthesis support structure 330.

Valve prosthesis 300 further includes a motion limiting member 324. Motion limiting member 324 includes a substantially rigid circular frame disposed around outflow section 320. The substantially rigid circular frame preferably substantially maintains its shape even when subjected to outside forces such as can be present within a body lumen of a patient. The substantially rigid circular frame can be made of, for example, the types of surgical steel traditionally used for making stent devices. Motion limiting member 324 can be mounted to valve prosthesis support structure 330 by being attached to distal ends of posts 322. In such a configuration, motion limiting member 324 prevents divergence of posts 322 by limiting the maximum diameter of outflow section 320, thereby preventing motion of posts 322 beyond the limits imposed by motion limiting member 324. Motion limiting member 324 can be constructed of a variety of materials, for example, nitinol.

The rigid circular frame of motion limiting member 324 can, however, be sufficiently flexible to be compatible with collapse of valve prosthesis 300 during an insertion process.

The rigid circular frame of motion limiting member 324 can alternately or additionally be mounted to valve prosthesis support structure 330 by being attached to proximal ends of posts 322, or at intermediate positions of posts 322, in between proximal and distal ends.

Because the diameter of outflow section 320 is limited by motion limiting member 324, the diameter of outflow section 320 is not substantially affected by changes in the diameter of inflow section 310, thereby decoupling radial motion of outflow section 320 from radial interference at inflow section 310. Thus, valve prosthesis 300 maintains predictable and stable valve geometry regardless of patient-specific anatomy.

Figure 6:
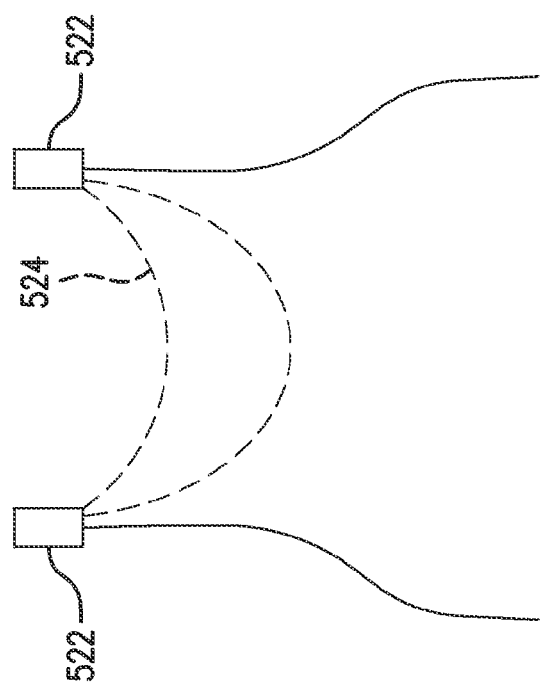
FIG. 6 is a side schematic view of the valve prosthesis of FIG. 5.
Figure 5:
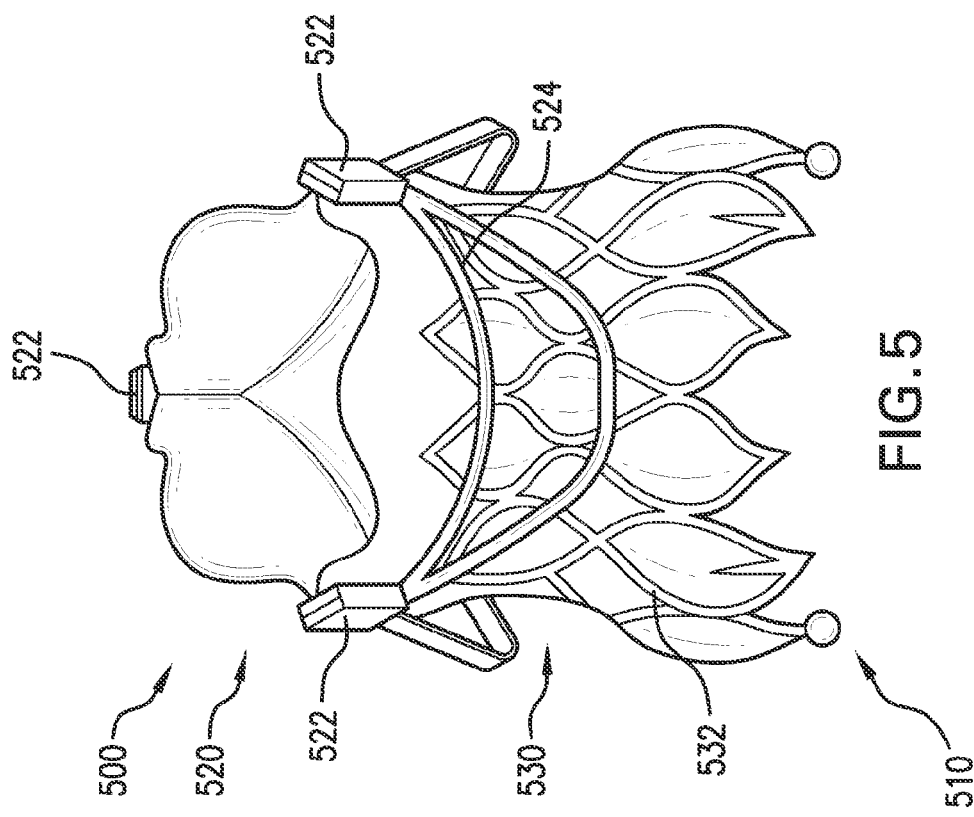
FIG. 5 is a perspective view of a valve prosthesis according to an embodiment of the present invention.

FIG. 5 is a perspective view of a valve prosthesis 500 according to an exemplary embodiment of the present invention. FIG. 6 is a side schematic view of valve prosthesis 500. Description of elements of the embodiment depicted in FIGS. 5 and 6 that are the same or operate similarly as the embodiments described above may be omitted or abbreviated.

Valve prosthesis 500 includes an inflow section 510 at a proximal end thereof, and an outflow section 520 at a distal end thereof. Valve prosthesis 500 also includes a valve prosthesis support structure 530, and a motion limiting member 524. Valve prosthesis support structure 530 includes posts 522 proximate to outflow section 520, and a proximal skirt 532 extending from inflow section 510 toward posts 522.

Motion limiting member 524 includes rigid arches disposed proximate to outflow section 520. Each rigid arch is mounted to valve prosthesis support structure 530 by being attached to proximal ends of two adjacent posts 522. In this way, the rigid arches of the motion limiting member 524 together extend around outflow section 520. In such a configuration, motion limiting member 524 prevents divergence of posts 522 by limiting the diameter of outflow section 520, thereby preventing motion of posts 522 beyond the limits imposed by motion limiting member 524.

In some embodiments, the rigid arches of motion limiting member 524 can together form a circular shape, or can form another shape, such as, for example, a series of linked "humps" connecting around outflow section 520.

In some embodiments, the rigid arches of motion limiting member 524 are sufficiently flexible to collapse with valve prosthesis 500 during an insertion process.

In some embodiments, the rigid arches of motion limiting member 524 are mounted to valve prosthesis support structure 530 by being attached to distal ends of posts 522, or at intermediate positions of posts 522, in between proximal and distal ends.

In some embodiments, the rigid arches of motion limiting member 524 can extend out from valve prosthesis support structure 530 at a 90 degree angle with respect to a longitudinal axis extending through valve prosthesis 500. Alternatively, the rigid arches of motion limiting member 524 can extend from valve prosthesis support structure 530 at an angle other than 90 degrees, such as, for example, approximately 30 degrees, approximately 45 degrees, or approximately 120 degrees. Moreover, each rigid arch need not extend out from valve prosthesis support structure 530 at the same angle as other rigid arches.

In some embodiments multiple rigid arches can extend between adjacent posts 522. Intermediate connections can be formed between adjacent rigid arches such that the rigid arches extending between adjacent posts 522 are connected in series.

Because the diameter of outflow section 520 is limited by motion limiting member 524, it is not substantially affected by radial interference (i.e., changes in diameter) at inflow section 510, thereby achieving decoupling of radial motion of outflow section 520 from radial interference at inflow section 510. Thus, valve prosthesis 500 maintains predictable and stable valve geometry regardless of patient-specific anatomy.

Figure 8:
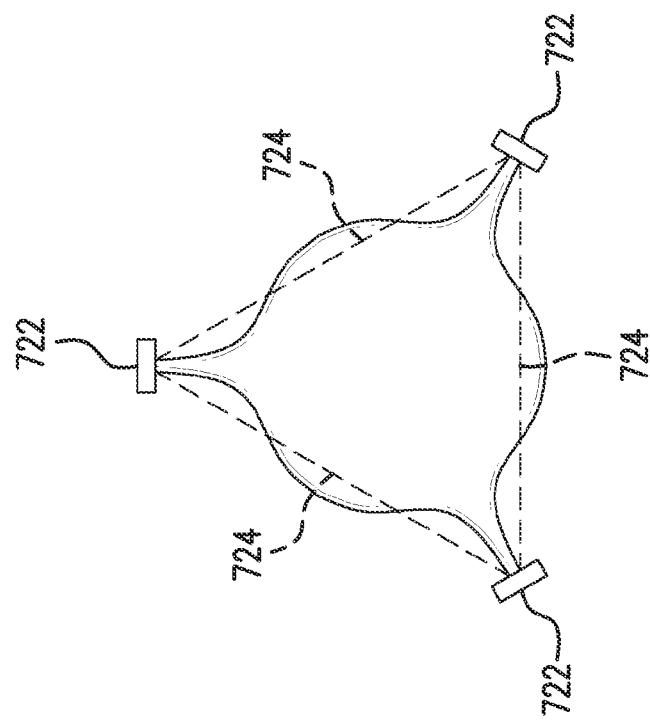
FIG. 8 is a top schematic view of the valve prosthesis of FIG. 7.
Figure 7:
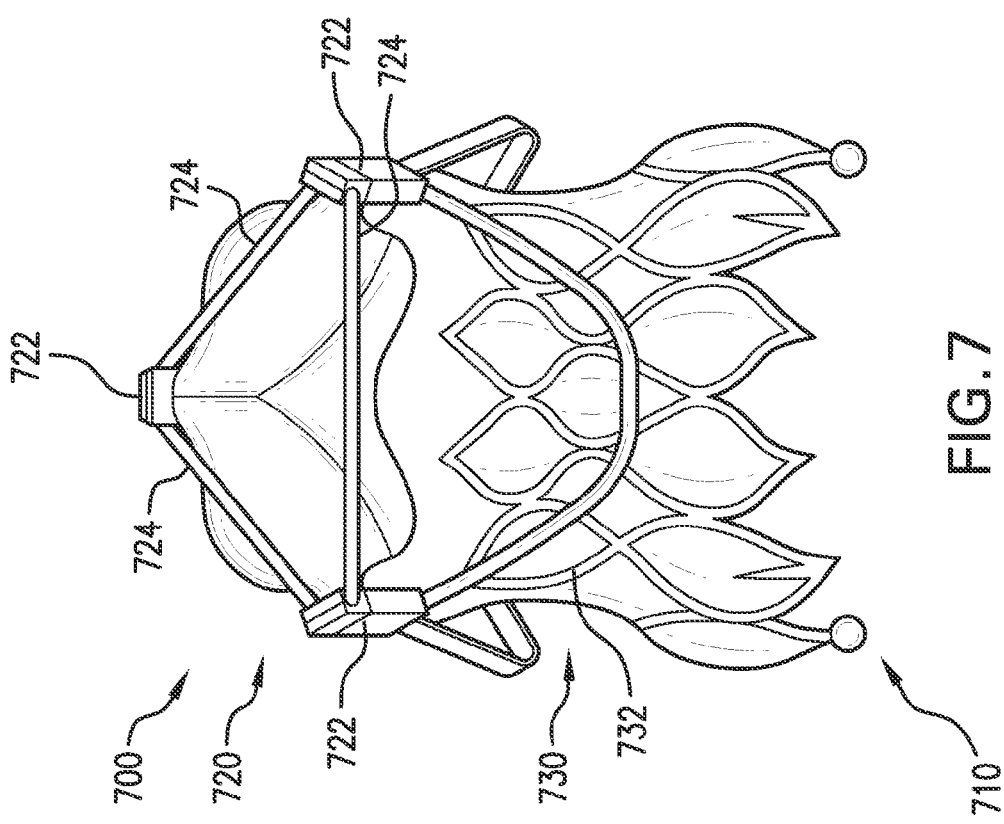
FIG. 7 is a perspective view of a valve prosthesis according to an embodiment of the present invention.

FIG. 7 is a perspective view of a valve prosthesis 700 according to an embodiment of the present invention. FIG. 8 is a side schematic view of valve prosthesis 700. Description of elements of the embodiment depicted in FIGS. 7 and 8 that are the same or operate similarly as the embodiments described above may be omitted or abbreviated.

Valve prosthesis 700 includes an inflow section 710 at a proximal end thereof, and an outflow section 720 at a distal end thereof. Valve prosthesis 700 also includes a valve prosthesis support structure 730, and a motion limiting member 724.

Valve prosthesis support structure 730 includes posts 722 proximate to outflow section 720, and a proximal skirt 732 extending from posts 722 toward inflow section 710.

Motion limiting member 724 includes linear support elements disposed proximate to outflow section 720. Each linear support element is mounted to valve prosthesis support structure 730 by being attached to distal ends of two adjacent posts 722. In this way, the linear support elements of motion limiting member 724 together link posts 722. In such a configuration, motion limiting member 724 prevents divergence of posts 722 by limiting the diameter of outflow section 720, thereby preventing motion of posts 722 beyond the limits imposed by motion limiting member 724.

In some embodiments the linear support elements of motion limiting member 724 are non-rigid and act only in tension. For example, such linear support elements can be made of string, wire, sutures, or the like.

In some embodiments, the linear support elements of motion limiting member 724 are rigid.

In some embodiments, the linear support elements of motion limiting member 724 are mounted to valve prosthesis support structure 730 by being attached to proximal ends of posts 722, or at intermediate positions of posts 722, in between proximal and distal ends.

In some embodiments multiple linear support sub-elements can extend between adjacent posts 722, with intermediate connections between adjacent linear support sub-elements such that the linear support sub-elements extending between adjacent posts 722 are connected in series.

Because the diameter of outflow section 720 is limited by motion limiting member 724, it is preferably not substantially affected by radial interference (i.e., changes in diameter) at inflow section 710, thereby achieving decoupling of radial motion of outflow section 720 from radial interference at inflow section 710. Thus, valve prosthesis 700 maintains predictable and stable valve geometry regardless of patient-specific anatomy.

Figure 10:
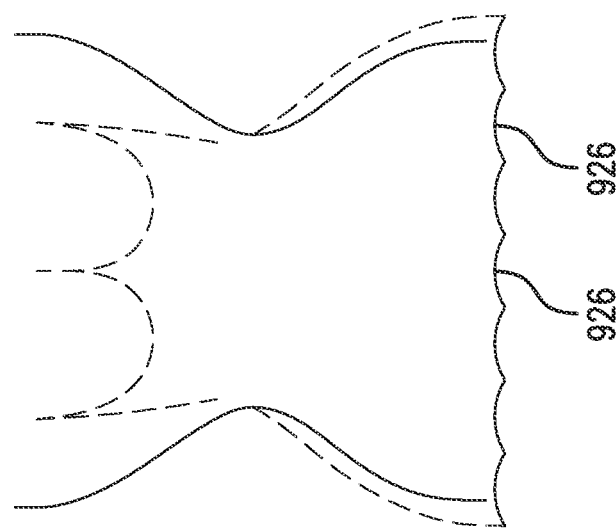
FIG. 10 is a side schematic view of the valve prosthesis of FIG. 10.
Figure 9:
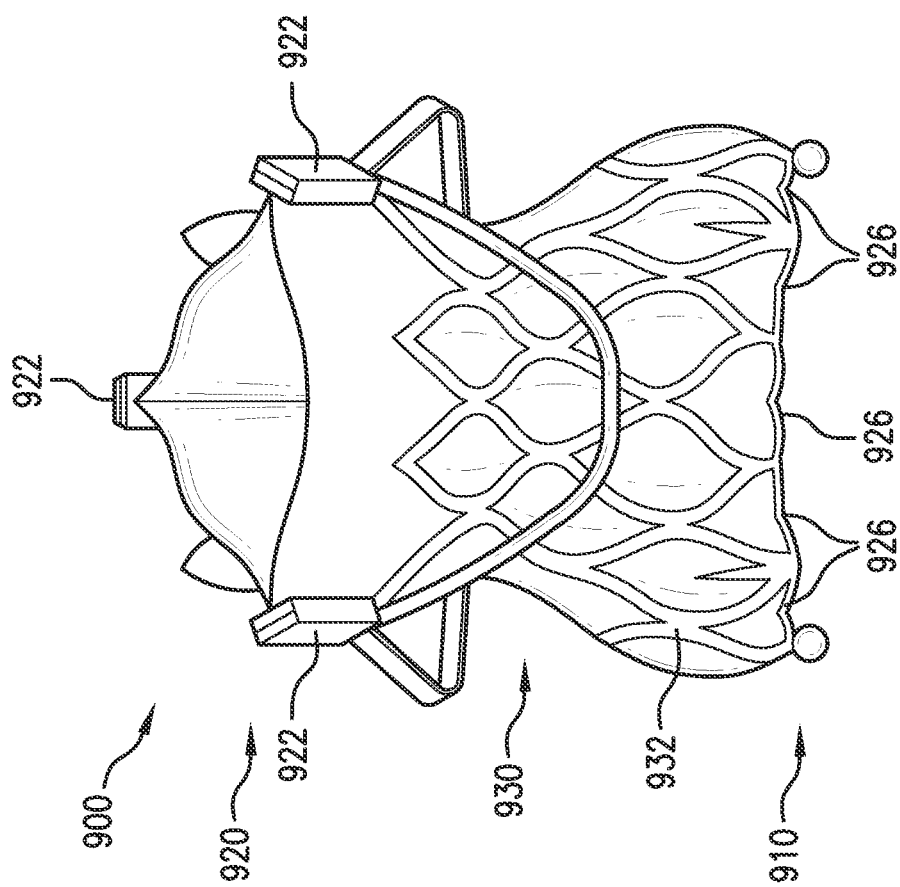
FIG. 9 is a perspective view of a valve prosthesis according to an embodiment of the present invention.

FIG. 9 is a perspective view of a valve prosthesis 900 according to an embodiment of the present invention. FIG. 10 is a side schematic view of valve prosthesis 900. Description of elements of the embodiment depicted in FIGS. 9 and 10 that are the same or operate similarly as the embodiments described above may be omitted or abbreviated.

Valve prosthesis 900 includes an inflow section 910 at a proximal end thereof, and an outflow section 920 at a distal end thereof. Valve prosthesis 900 also includes a valve prosthesis support structure 930, and a motion limiting member 926.

Valve prosthesis support structure 930 includes posts 922 proximate to outflow section 920, and a proximal skirt 932 extending from inflow section 910 toward posts 922.

Motion limiting member 926 includes strut support elements disposed proximate to inflow section 910. Each strut support element is mounted to a proximal end of inflow section 910, and extends between adjacent endpoints of proximal skirt 932. In this way, the strut support elements of motion limiting member 926 together link endpoints of inflow section 910. In such a configuration, motion limiting member 926 prevents divergence of the endpoints of proximal skirt 932 by limiting the diameter of inflow section 910, thereby preventing motion of the endpoints of proximal skirt 932 beyond the limits imposed by motion limiting member 926.

In some embodiments, multiple strut support elements can extend between adjacent endpoints of proximal skirt 932, with intermediate connections between adjacent endpoints of proximal skirt 932 such that the strut support elements extending between adjacent endpoints of proximal skirt 932 are connected in series.

In some embodiments, the strut support members of motion limiting member 926 are incorporated in and form a part of proximal skirt 932 such that motion limiting member 926 and proximal skirt 932 are formed together monolithically.

In some embodiments, the strut support members of motion limiting member 926 are rigid. In some embodiments, the strut support members of motion limiting member are non-rigid.

Because the diameter of inflow section 910 is limited by motion limiting member 926, its motion due to valve function and cardiac contraction can be confined to within limits necessary for proper functioning, thereby eliminating or reducing unnecessary radial movement. Reducing this unnecessary radial movement in turn reduces the fatigue that valve prosthesis 900 is subject to, thereby extending its useful life, and eliminating the need for subsequent replacement of valve prosthesis 900 or reducing the frequency with which valve prosthesis 900 must be replaced to maintain proper functionality. Additionally, because motion limiting member 926 limits the diameter of inflow section 910, valve prosthesis 900 maintains more predictable and stable valve motion and valve geometry regardless of patient-specific anatomy. Further, stabilizing the diameter of inflow section 910 results in less deformation (i.e., changes in diameter) of outflow section 920.

Figure 11:
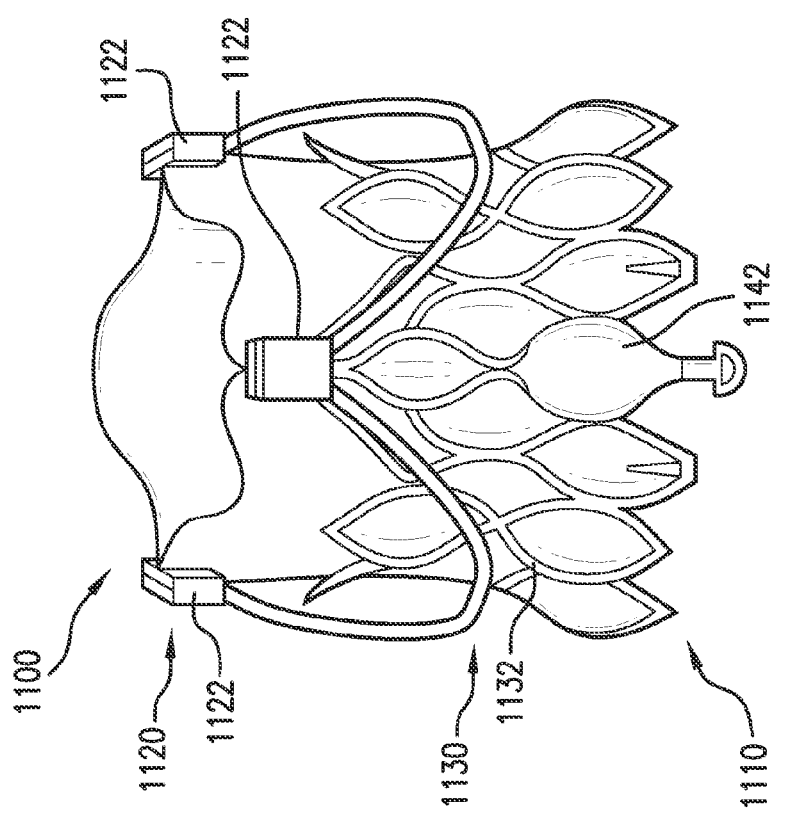
FIG. 11 is a perspective view of a valve prosthesis according to an embodiment of the present invention.

FIG. 11 is a perspective view of a valve prosthesis 1100 according to an embodiment of the present invention. Description of elements of the embodiment depicted in FIG. 11 that are the same or operate similarly as those described above may be omitted or abbreviated.

Valve prosthesis 1100 includes an inflow section 1110 at a proximal end thereof, and an outflow section 1120 at a distal end thereof. Valve prosthesis 1100 also includes a valve prosthesis support structure 1130, and sealing members 1142.

Valve prosthesis support structure 1130 includes posts 1122 proximate to outflow section 1120, and a proximal skirt 1132 extending from posts 1122 toward inflow section 1110.

Sealing members 1142 can be disposed proximate to inflow section 1110, and can be positioned to correspond radially with posts 1122. Such positioning corresponds to native commissures, and aligns sealing members 1142 with a patient's inter-leaflet triangles. Sealing members 1142 can be shaped so as to fit into the inter-leaflet triangles, or can be formed of a material that conforms to the shape of the inter-leaflet triangles upon being placed in contact with the inter-leaflet triangles. In this way, sealing members 1142 help valve prosthesis 1100 attain a high level of conformance to the patient's annular anatomy, thereby preventing or reducing the chance and severity of paravalvular leakage. U.S. application Ser. No. 13/091,765, filed Apr. 21, 2011, discusses sealing members for use with prosthetic valves, and is incorporated by reference herein in its entirety.

Figure 12:
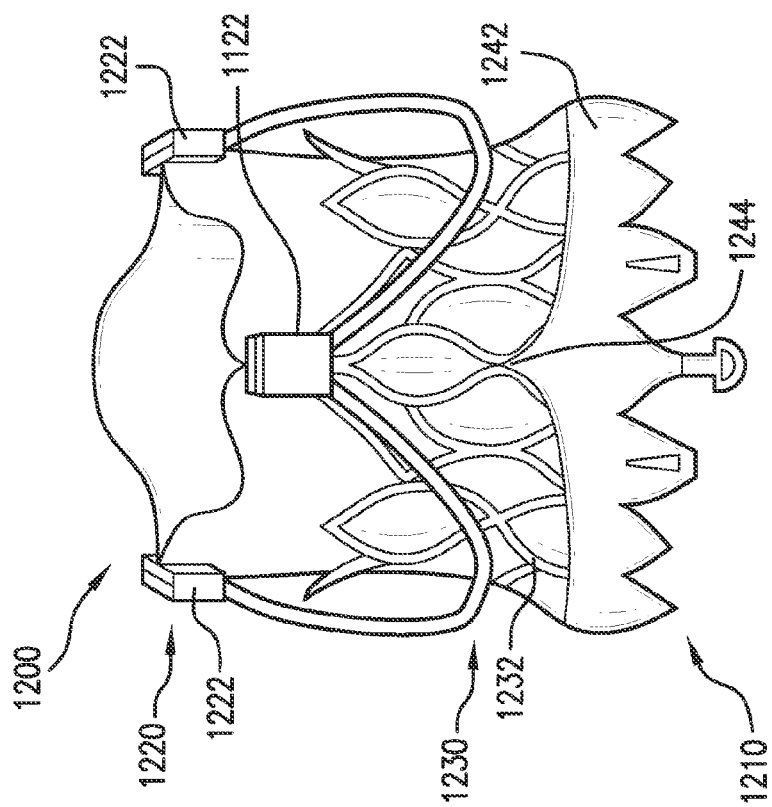
FIG. 12 is a perspective view of a valve prosthesis according to an embodiment of the present invention.

FIG. 12 is a perspective view of a valve prosthesis 1200 according to an embodiment of the present invention. Description of elements of the embodiment depicted in FIG. 12 that are the same or operate similarly as those described above may be omitted or abbreviated.

Valve prosthesis 1200 includes an inflow section 1210 at a proximal end thereof, and an outflow section 1220 at a distal end thereof. Valve prosthesis 1200 also includes a valve prosthesis support structure 1230, and a sealing member 1242.

Valve prosthesis support structure 1230 includes posts 1222 proximate to outflow section 1220, and a proximal skirt 1232 extending from posts 1222 toward inflow section 1210.

Sealing member 1242 can be disposed proximate to inflow section 1210, and can extend around the circumference of proximal skirt 1232. Sealing member 1242 can include sealing tips 1244 positioned to correspond radially with posts 1222. Such positioning corresponds to native commissures, and aligns sealing tips 1244 with a patient's inter-leaflet triangles. Sealing tips 1244 can be shaped so as to fit into the inter-leaflet triangles, or can be formed of a material that conforms to the shape of the inter-leaflet triangles upon being placed in contact with the inter-leaflet triangles. In this way, sealing member 1242, including sealing tips 1244, helps valve prosthesis 1200 attain a high level of conformance to the patient's annular anatomy, thereby preventing or reducing the chance and severity of paravalvular leakage.

In some embodiments, sealing member 1242 including sealing tips 1244 is formed of a single material. In some embodiments, sealing tips 1244 are formed of a material different from the balance of sealing member 1242. For example, sealing tips 1244 can be formed of a soft material capable of conforming to the patient's inter-leaflet triangles, while the balance of sealing member 1242 can be formed of a more rigid material.

In some embodiments, sealing member 1242 acts as a motion limiting member, and limits the diameter of inflow section 1210, thereby preventing motion of endpoints of proximal skirt 1232 beyond limits imposed by sealing member 1242. In this way, sealing member 1242 is similar to motion limiting member 926.

While various embodiments of the present invention have been described above, they have been presented by way of example only, and not limitation. The elements of the embodiments presented above are not necessarily mutually exclusive, but can be interchanged to meet various needs as would be appreciated by one of skill in the art.

It therefore will be apparent to one skilled in the art that various changes in form and detail can be made to the embodiments disclosed herein without departing from the spirit and scope of the present invention. The phraseology or terminology herein is used for description and not for limitation. Thus, it is intended that the present invention cover modifications and variations of this invention provided they come within the scope of the appended claims and their equivalents.

What is claimed is:

1. A prosthesis comprising:
    a support structure having an inflow section and an outflow section; and
    a motion limiting member coupled to the outflow section of the support structure,
    wherein radial motion of the outflow section is decoupled from radial interference at the inflow section by the motion limiting member.

2. The prosthesis of claim 1, wherein the deployed diameter of the inflow section is variable, and
    wherein the deployed diameter of the outflow section is constant at any deployed inflow section diameter.

* * * * *